United States Patent
Macrides et al.

(12) 
(10) Patent No.: US 6,346,278 B1
(45) Date of Patent: *Feb. 12, 2002

(54) LIPID EXTRACT HAVING ANTI-INFLAMMATORY ACTIVITY

(75) Inventors: Theodore Macrides, Lower Templestowe; Nicolette Kalafatis, East Prahran, both of (AU)

(73) Assignee: Pharmalink International Limited, Hong Kong (HK)

( * ) Notice: Subject to any disclaimer, the term of this patent is extended or adjusted under 35 U.S.C. 154(b) by 0 days.

This patent is subject to a terminal disclaimer.

(21) Appl. No.: 09/610,484

(22) Filed: Jul. 5, 2000

Related U.S. Application Data

(63) Continuation of application No. 09/029,957, filed as application No. PCT/AU96/00564 on Sep. 10, 1996, now Pat. No. 6,083,536.

(30) Foreign Application Priority Data

Sep. 11, 1995 (AU) .............................................. PN 5311

(51) Int. Cl.[7] .............................................. A61K 35/56
(52) U.S. Cl. ........................ 424/547; 424/520; 424/522; 424/523
(58) Field of Search ................................. 424/547, 520, 424/522, 523

(56) References Cited

U.S. PATENT DOCUMENTS

| | | |
|---|---|---|
| 4,455,298 A | 6/1984 | McFarlane et al. |
| 4,801,453 A | 1/1989 | Kosuge et al. |
| 6,083,536 A * | 7/2000 | Macrides et al. |

FOREIGN PATENT DOCUMENTS

WO  WO 96/05164  2/1996

OTHER PUBLICATIONS

Leung and Stefano, PNAS. 81(3), pp. 955–958, Mar. 1984.
Leung and Stefano, Life Sciences, 33 Suppl 1., pp. 77–80, 1983.
Arzneimittel Forschung/Drug Research, vol. 30, No. (ii), 1980, Editio Cantor, Aulendorft, Germany, K.D. Rainsford et al. "Gastroprotective and Anti–inflammatory Properties of Green Lipped Mussel (Pera canaliculus) Preparation," pp. 2128–2132.
Chemical and Pharmaceutical Bulletin, vol. 34, No. 11, 1986, Pharmaceutical Society of Japan, Tokyo, Takuo Kosuge et al., "Isolation of an Anti–histiminic Substance from Green Lipped Mussel (Perna canaliculus)," pp. 4825–4828.
Derwent Abstract Accession No. 89–333329/46, DE, 3814047, C (Fratzer) Nov. 16, 1989.
Agents and Actions, vol. 39 (Spec. Conf. Issue), 1993, Basel, Switzerland, Miller, T.E. et al., "Anti–inflammatory activity of glycogen extracted from Perna canaliculus (NZ green–lipped mussel)," pp. C139–142.
New Zealand Medical Journal, vol. 95, No. 720, 1982, Dunedin, New Zealand, Crouch, R.A.F. et al., "Anti–inflammatory activity in fractionated extracts of the green–lipped mussel," pp. 803–806.

* cited by examiner

Primary Examiner—Leon B. Lankford, Jr.
(74) Attorney, Agent, or Firm—Pillsbury Winthrop LLP

(57) ABSTRACT

Anti-inflammatory, and particularly anti-arthritic, treatment of a human or animal patient comprises administration to the patient of an effective amount of a lipid extract of *Perna canaliculus* or *Mytilus edulis*.

14 Claims, No Drawings

LIPID EXTRACT HAVING ANTI-INFLAMMATORY ACTIVITY

This is a continuation of U.S. application Ser. No. 09/029,957, filed May 5, 1998, now U.S. Pat. No. 6,083,536, a national phase filing based on PCT/AU96/00564, filed Sep. 10, 1996, priority benefit based on said earlier filings as well as Australian Appln. No. 5311/95, filed Sep. 11, 1995 being claimed herein.

FIELD OF THE INVENTION

This invention relates in general to a preparation having anti-inflammatory, and particularly anti-arthritic, activity which is a lipid extract of mussels, including the New Zealand green lipped mussel, *Perna canaliculus*, and the blue mussel *Mytilus edulis*.

BACKGROUND OF THE INVENTION

There is at the present time a significant medical need for new anti-inflammatory and anti-arthritic drugs with reduced side effects and prolonged in vivo activity and in particular for compounds which will moderate the progress of the arthropathies. Plants and other living cells offer a vast reservoir of compounds which have pharmacological effects on humans. Natural products have frequently been the source of effective drugs and lately there has been an increased interest in the analysis of these natural products, especially where a clinical benefit is claimed. Marine organisms contain metabolites that can act as pharmacological agents and aid in the treatment of inflammation.

An anti-inflammatory activity of *Perna canaliculus* (New Zealand Green Lipped Mussel) was first implicated as part of a pharmacological study on leukaemia. Initial assessment of the anti-inflammatory activity of *Perna canaliculus* was first attempted using a polyarthritis model in rats[1]. These studies however failed to show the presence of any significant anti-inflammatory activity in the mussel preparation. In contrast, Miller and Ormrod[2] using a carrageenin-induced paw oedema assay[3], were able to show that mussel preparations, when administered intraperitoneally, gave a significant reduction in the swelling of a carrageenin-induced rat paw oedema. Subsequently, they fractionated a non-dialysable, water-soluble fraction from the mussel preparation that possessed anti-inflammatory activity. The aqueous extract showed a dose-ependent anti-inflammatory activity when administered intraperitoneally and could not be detected upon oral administration of the mussel powder. It was suggested that the water-soluble fraction therefore contained an irritant component possessing apparent anti-inflammatory activity.

Rainsford and Whitehouse[4] also reported that freeze-dried powdered preparations of the whole mussel given orally to rats showed some modest anti-inflammatory activity in the carrageenin-induced paw oedema assay, and that this material strikingly reduced the gastric ulcerogenicity of several non-steroidal anti-inflammatory drugs in rats and pigs.

Use of the whole mussel extract in the treatment of both rheumatoid arthritis and osteoarthritis in human patients has also been reported[5].

Initial work leading to the present invention based on lipid extracts from *Perna canaliculus* powder prepared using solvent extraction techniques (in contrast to earlier work on aqueous fractions), established that the lipid fractions show a measure of anti-inflammatory activity when tested in appropriate model systems. A reliable source of lipid extract of *Perna canaliculus* and *Mytilus edulis* has subsequently become available through the procedure of supercritical fluid extraction (SFE). The lipid extract is obtained as a dark yellow-brown viscous oil exhibiting strong ultraviolet absorbing character which is consistent in physical data to lipid extracts obtained from earlier solvent extraction procedures.

SUMMARY OF THE INVENTION

Accordingly to one aspect, the present invention provides a method of anti-inflammatory treatment of a human or animal patient, which comprises administration to the patient of an effective amount of a lipid extract of *Perna canaliculus* or *Mytilus edulis*.

In another aspect, the present invention provides an anti-inflammatory composition comprising a lipid extract of *Perna canaliculus* or *Mytilus edulis* as an active component thereof, together with one or more pharmaceutically acceptable carriers and/or diluents.

In yet another aspect, the invention extends to the use of a lipid extract of *Perna canaliculus* or *Mytilus edulis* in the preparation of a composition for anti-inflammatory treatment of a human or animal patient.

DETAILED DESCRIPTION OF THE INVENTION

The terms "anti-inflammatory treatment" and "anti-inflammatory composition" as used herein, relate to treatment of, or compositions for treatment of inflammatory conditions in general, including arthritic conditions such as osteoarthritis and rheumatoid arthritis, as well as in treatment of multiple sclerosis and various viral infections. Activity of a compound for use in such treatment may be demonstrated using standard assays, for example using a carrageenin-induced paw oedema assay or by the ability to beneficially limit the onset or progression of an experimental polyarthritis, as described in detail herein.

Preferably, the lipid extract which is used in the treatment or composition of the present invention is an extract prepared by supercritical fluid extraction (SFE) of freeze-dried powdered mussel using a cryogenic fluid (such as cryogenic fluid $CO_2$) as the extracting medium. In comparison to solvent extraction techniques, supercritical fluid extraction using cryogenic fluid $CO_2$ produces a lipid extract rich in non-polar lipids, particularly in free fatty acids. While the exact composition of the lipid extract has not yet been established, it is known to contain not only free fatty acids (including unsaturated fatty acids), but also triglycerides and cholesterol esters.

A variety of administration routines are available. The particular mode selected will depend, of course, upon the particular condition being treated and the dosage required for therapeutic efficacy. The methods of this invention, generally speaking, may be practised using any mode of administration that is medically acceptable, meaning any mode that produces therapeutic levels of the active component of the invention without causing clinically unacceptable adverse effects. Such modes of administration include oral, rectal, topical, nasal, transdermal or parenteral (e.g. subcutaneous, intramuscular and intravenous) routes. In particular, the lipid extract of the present invention has been found to be active when administered orally, subcutaneously and transdermally.

Transdermal administration of the lipid extract is a particularly preferred administration mode, as the lipid extract has been found to have surprising anti-inflammatory activity when administered transdermally.

The compositions of this invention may conveniently be presented in unit dosage form and may be prepared by any of the methods well known in the art of pharmacy. Such methods include the step of bringing the active component into association with a carrier which constitutes one or more accessory ingredients. In general, the compositions are prepared by uniformly and intimately bringing the active component into association with a liquid carrier, a finely divided solid carrier, or both, and then, if necessary, shaping the product.

Compositions of the present invention suitable for oral administration may be presented as discrete units such as capsules, cachets, tablets or lozenges, each containing a predetermined amount of the active component, in liposomes or as a suspension in an aqueous liquid or non-liquid such as a syrup, an elixir, or an emulsion.

Compositions suitable for parenteral administration conveniently comprise a sterile aqueous preparation of the active component which is preferably isotonic with the blood of the recipient. This aqueous preparation may be formulated according to known methods using those suitable dispersing or wetting agents and suspending agents. A sterile injectable preparation may be formulated as a sterile injectable solution or suspension in a nontoxic parenterally-acceptable diluent or solvent, for example as a solution in polyethylene glycol and lactic acid. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono-or di-glycerides. In addition, fatty acids such as oleic acid find use in the preparation of injectables.

Compositions suitable for transdermal administration conveniently comprise the active component in an ointment or lotion base or vehicle, and may include a skin penetration enhancing agent to assist in administration of the active component. Suitable bases or vehicles are oils such as olive or emu oil, administered alone or with a penetrant such as cineole or limonene.

Other delivery systems can include sustained release delivery systems. Preferred sustained release delivery systems are those which can provide for release of the active component of the invention in sustained release pellets or capsules. Many types of sustained release delivery systems are available. These include, but are not limited to: (a) erosional systems in which the active component is contain within a matrix, and (b) diffusional systems in which the active component permeates at a controlled rate through a polymer.

The formulation of such therapeutic compositions is well known to persons skilled in this field. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and it is described, by way of example in *Remington's Pharmaceutical Sciences*, 18th Edition, Mack Publishing Company, Pennsylvania, USA. Except insofar as any conventional media or agent is incompatible with the active component, use thereof in the pharmaceutical compositions of the present invention is contemplated. Supplementary active ingredients can also be incorporated into the compositions.

Oral or transdermal administration will be preferred for many conditions because of the convenience to the patient, although localised sustained delivery may be more desirable for certain treatment regimens.

The active component is administered in therapeutically effective amounts. A therapeutically effective amount means that amount necessary at least partly to attain the desired effect, or to delay the onset of, inhibit the progression of, or halt altogether, the onset or progression of the particular condition being treated. Such amounts will depend, of course, on the particular condition being treated, the severity of the conditions and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgement. It will be understood by those of ordinary skill in the art, however, that a lower dose or tolerable dose may be administered for medical reasons, psychological reasons or for virtually any other reasons.

It is especially advantageous to formulate compositions in dosage unit form for ease of administration and uniformity of dosage. Dosage unit form as used herein refers to physically discrete units suited as unitary dosages for the human or animal patients to be treated; each unit containing a predetermined quantity of active component calculated to produce the desired therapeutic effect in association with the required pharmaceutical carrier and/or diluent. The specifications for the novel dosage unit forms of the invention are dictated by and directly dependent on (a) the unique characteristics of the active component and the particular therapeutic effect to be achieved, and (b) the limitations inherent in the art of compounding such an active component for the particular treatment.

Generally, daily doses of active component will be from about 0.01 mg/kg per day to 1000 mg/kg per day. Small doses (0.01–1 mg) may be administered initially, followed by increasing doses up to about 1000 mg/kg per day. In the event that the response in a subject is insufficient at such doses, even higher doses (or effective higher doses by a different, more localised delivery route) may be employed to the extent patient tolerance permits. Multiple doses per day are contemplated to achieve appropriate systemic levels of the active component.

Throughout this specification unless the context requires otherwise, the word "comprise", or variations such as "comprises" or "comprising", will be understood to imply the inclusion of a stated integer or group of integers but not the exclusion of any other integer or group of integers.

Further features of the present invention are more fully described in the following Example(s). It is to be understood, however, that this detailed description is included solely for the purposes of exemplifying the present invention, and should not be understood in any way as a restriction on the broad description of the invention as set out above.

EXAMPLE 1

A PREPARATION OF LIPID EXTRACT

A.1 Raw Material

The green lipped mussel (*Perna canaliculus*) is harvested on the south coast of New Zealand at which time the total mussel is stabilised with tartaric acid. Freeze drying results in a dry power of pulverised form.

A.2 Extraction of Lipids

The technique of supercritical fluid extraction (SFE) is utilised to extract the biologically active lipids from the crude mussel powder. Cryogenic fluid $CO_2$ is used as the extracting medium. The $CO_2$ is expanded to atmospheric pressure and the extract is presented as a concentrated oil. The powder yields 3–3.5% of oil.

A.3 Profile of the crude oil

The extractable oil is orange amber in colour and is a viscous liquid at ambient temperature. The extract is stored below 4° C. and is handled in a nitrogen atmosphere. The crude oil shows strong UV activity and is protected from light to minimise the polymerisation of double bond components.

PILOT SCALE SUPERCRITICAL FLUID EXTRACTION

Extraction of total lipids in freeze-dried mussel powder, *Perna canaliculus* was performed on a pilot scale SFE unit undertaken at the Food Research Institute (Department of Agriculture, Werribee, Vic., Australia).

B.1 Instrumentation

Extractions were performed on a pilot scale extraction unit consisting of five basic sub-units (Distillers MG Limited., England, UK). The five basic units comprise: Carbon dioxide supply, Solids extraction, Primary separation, Evaporation and Tailing units.

The carbon dioxide supply unit consists of two $CO_2$ cylinders connected in parallel and placed on a weighing scale for recharging when appropriate. The extraction unit can be supplied with liquid $SC—CO_2$ and $SC—CO_2$. For this work the SFE unit was operated using $SC—CO_2$. Solid material was placed in the leaching column and the primary separator facilitates separation of extracted material by reduction of pressure (which allows extract to settle), adsorption or liquid extraction. The fluid extract was passed into the evaporation unit to evaporate the $CO_2$ by the use of internal heating tubes. The vapour may contain volatiles and thus it is subsequently passed to the tailing column to be scrubbed by pure liquid $CO_2$. The tailing unit traps the gaseous $CO_2$ from the evaporator unit and returns the volatile components to the evaporator.

B.2 Pilot plant extraction procedure

Mussel power (300 g) was charged to the extraction unit (leaching column). $SC—CO_2$ was delivered at a flow rate of 3.0 kg/h for two hours per extraction. Extractor temperature was set at 40° C. and the extractor pressure at 310 bar (4,500 psi). The evaporator temperature was held constant at 40° C. The mussel lipid extracts were stored under nitrogen at −10° C. In amber glass sealed containers.

EXAMPLE 2

Lipid extract of *Perna canaliculus* (herein referred to as "PCO") prepared by SFE as described in Example 1 was assayed for acute anti-inflammatory activity in the standard carrageenin rat oedema assay, as well as for anti-arthritic activity (measuring activity in suppressing chronic inflammation) against experimentally induced polyarthritis in rats[6].

Comparative tests were carried out with Seatone™, a commercially available freeze dried powder preparation of *Perna canaliculus*.

A. METHODS

PCO was kept at −20° C. Traces of hexane etc. were not removed before use. Formulations were aged no more than 24 hours at 4° C.

A.1 Anti-inflammatory Assay

Female Wistar rats (180–220 gm) were pre-dosed p.o. or i.p. with test formulations. 40 minutes later they were injected in each rear paw with 0.1 ml saline containing 0.6 mg Na carrageenin. The subsequent paw oedema was quantified by measuring the increase in paw thickness after one and two hours with a screw gauge micrometer. The $ED_{50}$ for aspirin is approximately 150 mg/kg in this acute assay. [The oedema recedes after three hours with this dose of carrageenin.]

A.2 Anti-Arthritic Assay

Though more time consuming, this assay is of more value than the acute assay (described above) as it detects not only (i) those anti-inflammatory drugs acting in the acute assay (but often at lower $ED_{50}$ values) but also (ii) other agents e.g. clobuzarit ($CloZic^R$) or lobenzarit (CCA), which obviously have unique arthritis-suppressant properties but are not anti-oedemic/antipyretic or otherwise detectable in acute assays.

The protocol used is to pre-establish disease by injecting the arthritigen on Day 0, look for first signs of paw inflammation (usually manifest on Days 10–12) and then dose the animals with test materials for four days. Over this period, the paw inflammation in the untreated control animals "blooms" rapidly to reach a near maximum on Day 14. Drugs acting over this time-frame to hold down the paw swelling are certainly anti-symptomatic but rarely disease-ablating. On ceasing treatment, there is usually a recrudescence in symptoms. This however is a positive feature of this assay as it clearly indicates a) the drug has a finite action but gives some idea of its duration of efficacy by the rapidity (or otherwise) of the rebound; and b) the animals with minimal signs of disease on Day 14 reflected a positive drug effect rather than failure to respond to the original arthritigen (i.e. false negatives). An accurate description of this assay is "late prophylaxis". Obviously by delaying treatment until after Day 14, one can look for "therapeutic activity", but since changes may be slow or negligible within four days (even with some powerful NSAIDs), collection of adequate data is difficult.

Details of the protocol used are: inject the arthritigen into the tailbase of female Wistar rats (160–200 gm)=800 mcg heat-killed *Mycobact tuberculosis* suspended in 0.1 ml squalane in such a fashion as to avoid any blood vessels and to promote optimal drainage into the lymphatics. Ten days later, the animals were weighed, the thickness of the rear paws and tail was measured and signs of inflammation in the forepaws scored on a scale of 0 to 4 +. After dosing with test compounds once daily for four days (i.e. on Days 10 through 13 post-arthritigen), these measurements were repeated on Days 14 and 18 (i.e. after completion of treatment and again after four days rebound) to monitor the arthritis development. For transdermal administration of test formulations, animals were shaved over the back of the neck under light anaesthesia (Forthane) on Day 1 0, to expose an area of skin=ca.6cm². Formulations were applied once daily with rubbing for up to three minutes in a volume=2.5 ml/kg (i.e. approximately 0.5 ml/rat). The first application was given six hours after shaving to be sure there was no skin abrasions before treatment.

Antipyretic Assay

Young rats (less than 160 gm) were inoculated with 2 gm/kg dried brewer's yeast suspended in saline at 11 pm. At 8 am, their rectal temperatures were measured. Those showing a stable fever (temperature greater than 39.2° C.), at 9 am, were then dosed with test compounds. Paracetamol, 150 mg/kg was used for reference.

B. RESULTS

Acute Anti-inflammatory Activity (Table 1)

Table 1 indicates that neither Seatone nor PCO expressed anti-oedemic activity in the short-term assay. Co-administration with a synergist had no effect while amplifying that of Ibuprofen.

Anti-Arthritis Assay (Table 2)

Table 2 shows the results of the first two tests of PCO applied to arthritic rats either orally (p.o.) or subcutaneously (s.c.) or in a transdermal application (t.d.) at the one dose of 50 mg/kg given for four successive days.

Diluting PCO into refined commercial olive oil (Vetta) allowed the same stock solution to be tested in all three modes of delivery (p.o./s.c./t.d.). The olive oil (OO) base largely excludes oxygen and contains little metal catalyst and therefore has "keeping" properties for many unstable (unsaturated) compounds.

The transdermal formulations were prepared from the OO stock by adding skin penetration enhancers (PE) in the relatively high proportion of 20% v/v. The PE's used were cineole (=eucalyptol), methyl salicylate (=oil of wintergreen) or isopropanol (=rubbing alcohol). The PCO-salicylate group was perhaps the least responsive which might indicate some (negative) interaction between this salicylate ester and the active principle(s) of PCO.

TABLE 1

Anti-Inflammatory activity in the acute Carrageenin paw oedema.
n = 2 rats/group
MPL = Misoprostal, 0.5 mg/kg p.o. as synergist.

| mg/kg | Test Materials | MPL | % Inhibition Oedema 1 hr | 2 hr |
|---|---|---|---|---|
| 300 | SEATONE ®, p.o. | − | 08 | (−12)* |
|  |  | + | 15 | 20 |
| 50 | PCO-Tween, p.o. | − | 07 | 04 |
|  |  | + | (−04) | 02 |
|  | —, i.p. | − | (−12) | 06 |
|  |  | + | 04 | 15 |
| 30 | IBUPROFEN | − | 37 | 42 |
|  |  | + | 56 | 58 |

*(neg. values) = > controls

Conclusions:

(i) Both PCO and Seatone are inactive, even with synergist.

(ii) Assay responds to a standard NSAID and this particular synergist.

TABLE 2

Anti-Inflammatory activity in arthritic rats.
n = 4 rats/group.
Test compounds administered in 4 successive daily doses.
Mean increase in*

| Dose/kg | Treatment | Rear paw | Tail | Fore paw | Wt (gm) | % Inhib Rear | Front | Rebound** |
|---|---|---|---|---|---|---|---|---|
| A - Oral (p.o.) or Subcutaneous (s.c.) application: | | | | | | | | |
| — | None | 0.90 mm | 0.24 mm | 1.1+ | 05 | — | — | 0 |
| 2.5 ml | Olive oil, s.c. | 0.87 | 0.30 | + | 03 | 03% | 09% | 0 |
| 50 mg | PCO-Olive oil s.c. | 0.11 | 0.04 | 0.1+ | 10 | <u>88</u> | 91 | + |
|  | p.o. | 0.06 | −0.10 | 0.4+ | 05 | <u>93</u> | 64 | 2+ |
| 50 mg | PCO-Tween p.o. | 0.03 | −0.15 | 0.3+ | 09 | <u>97</u> | 83 | + |
| B = Transdermal application: | | | | | | | | |
| — | None | 1.08 | 0.17 | 1.5+ | 01 | — | — | 0 |
| 2.5 ml | Olive oil-Cineole | 0.96 | 0.05 | 1.4+ | 08 | 11% | 07% | 0 |
| 50 mg | PCO in 00-Cineole | 0.12 | −0.61 | 0 | 04 | <u>89</u> | 100 | 2+ |
|  | PCO in 00-Iso Pr OH | −0.01 | 0.09 | 0.1+ | −01 | <u>100</u> | 93 | 2+ |
|  | PCO in 00-Me Sal | 0.22 | 0.23 | 0.4+ | 05 | <u>80</u> | 73 | 2+ |

*over days 10 → 14
**over days 14 → 18
Vehicles = Olive oil, 4 vol:Penetrant, 1 vol.

Conclusions:

(i) PCO active at 50 mg/kg in 6 different modes of administration.

(ii) Vehicle controls (olive oil alone/with cineole) had insignificant effect on arthritis.

EXAMPLE 3

This Example sets out the results of further experiments on anti-arthritic and acute anti-inflammatory activity of the lipid extract of *Perna canaliculus* (PCO), showing it to be active down to 10 mg/kg, and possible even at 2.5 mg/kg, given either orally or transdermally in an olive oil vehicle.

Anti-arthritic Activity

Two experiments were set up to evaluate PCO at lower doses than the 50 mg/kg level found to show anti-inflammatory activity in arthritic rats when given p.o. or t.d. (see Example 2).

In the first experiment (Part A, Table 3) the olive oil formulation showed activity down to 2.5 mg/kg given orally. There was a significant rebound over the following four days, on ceasing dosing, in all three treatment groups.

In the second experiment (Part B, Table 3) using transdermal administration, the olive oil formulation "thinned" with 20% cineole (v/v) showed good activity down to 10 mg/kg. The result at 2.5 mg/kg is only provisional as it is not clear that there was a full "rebound" (possibly indicating some animals were "false-positives"=low reactors to the original arthritogen).

Alternative dermal formulations based on olive oil with 20% D-limonene or a non-oily vehicle (isopropanol with 20% v/v propylene glycol—this last being added to minimise skin dehydration) were clearly less satisfactory than the original olive oil-with-cineole delivery system. The alcohol vehicle would probably have facilitated decomposition of PCO in contrast to the olive oil.

Anti-inflammatory Activity

Kaolin-induced paw oedema was investigated as a possible assay for PCO since this inflammation is slower developing than that induced with carrageenin (which recedes after three hours). The protocol involves injecting 5 mg kaolin, suspended in water (not saline, in which it aggregates), into each rear paw 40 minutes after dosing the rats with PCO given both p.o. or i.p. as dispersions prepared with 0.02% Tween in either water (p.o.) or saline (i.p.). The paw swelling was then read two hours and five hours after the kaolin injection.

The results from one experiment (Table 4) with only two rats per group was ambiguous: the oral application may have provided some anti-oedemic activity. The i.p. PCO/saline emulsion was physically less satisfactory and seems to have been inactive.

Conclusions:
(i) PCO active at 10 mg/kg p.o. or t.d.
(ii) PCO may be active ever at 2.5 mg/kg
(iii) Cineole>Limonene for t.d. use with PCO
(iv) Non-oil vehicle seems inappropriate for t.d. delivery of PCO.

TABLE 4

Kaolin-induced paw oedema in female Wistar rats.
N = 2 rats/gp only
SYN = Synergist, Misoprostol @ 1 mg/kg p.o.

| Mg/kg | Treatment | Syn | % Inhibition Oedema | |
|---|---|---|---|---|
| | | | 2 HR | 5 HR |
| 150 | Aspirin p.o. | – | 55 | 51 |
| — | None | + | –15 | 07 |
| 50 | PCO, p.o. | + | 22 | 41? |
| 50 | PCO, i.p. | + | –10 | 09 |

Conclusions:
(i) PCO, p.o. may show delayed activity in this anti-inflammatory assay.
(ii) PCO, i.p. did not.

EXAMPLE 4

This Example demonstrates the effect of the lipid extract of *Perna canaliculus* (PCO) and various other oils available on the retail health food market when administered prophylactically to female Wistar rats developing adjuvant-induced polyarthritis (see Example 2). Treatment was carried out in six groups (n=5 rats per group) as follows:

A: Untreated control group
B: Flax Oil (Barleaus); 2000 mg/kg body weight/day.
C: Evening Primrose Oil (Efamol); 2000 mg/kg body weight/day.
D: Norwegian Salmon Oil (J. R.Carlson); 2000 mg/kg body weight/day.
E: MAXEPA (Solgar); 2000 mg/kg body weight/day.
F: PCO; 20 mg/kg body weight/day.

TABLE 3

Further studies of anti-inflammatory action of PCO in arthritic rats.
N = 4 rats/group

| Treatment | PCO (mg/kg) | Mean Swelling | | | Inhibition | |
|---|---|---|---|---|---|---|
| | | Rear paw | Tail | Front paw | Rear | Front |
| | | A. By oral administration. | | | | |
| None | | 1.37 mm | 0.14 mm | 1.5 + mm | — | — |
| PCO Olive oil | 25 | –0.12 mm | –0.24 mm | 0.2 + mm | 100% | 87% |
| | 10 | 0.04 mm | –0.41 mm | 0.5 + mm | 97% | 67% |
| | 2.5 | 0.40 mm | +0.23 mm | 0.5 + mm | 70% | 67% |
| | | B. By Dermal application. | | | | |
| Olive Oil-Cineole* | — | 0.82 mm | 0.06 mm | 0.8 + mm | — | — |
| | 25 | –0.12 mm | –0.27 mm | 0 | 100% | 100% |
| | 10 | 0.38 mm | –0.01 mm | –0.1 + mm | 54% | 100% |
| | 2.5 | 0.39 mm | –0.22 | +0.1 + mm | 52% | 87% |
| Olive Oil-Limonene* | 50 | 0.53 | 0.56 | 1.1 + mm | 35% | 0% |
| iPA-PrG** | 50 | 0.63 | 0.01 | 0.8 + mm | 23% | 0% |

*= 4:1 v/v, 2.5 ml/kg
**= 4 vol. Isopropanol with 1 vol. Propylene glycol.

The results are shown in Table 5 where the swelling of the arthritic paws is expressed as a percentage of the untreated control group A. These results show that PCO is 200× more potent than EPA, and 350× more potent than Evening Primrose Oil.

TABLE 5

| Group | Treatment | Increased paw diameter | % inhibition | Dose rate (mg/KG) |
|---|---|---|---|---|
| A | Untreated control group | 1.09 mm | 0% | 0 |
| B | Flax Oil | 1.07 mm | 2% | 2000 |
| C | Evening Primrose Oil | 0.82 mm | 25% | 2000 |
| D | Norwegian Salmon Oil | 0.74 mm | 32% | 2000 |
| E | MAXEPA | 0.55 mm | 50% | 2000 |
| F | PCO | 0.23 mm | 79% | 20 |

EXAMPLE 5

This Example shows therapeutic treatment of arthritis inflammation in rats using PCO, unstabilised whole mussel extract (GL Mussel NZ), stabilised whole mussel extract (GL Mussel Aust), celery seed oil and indomethacin. Rats with the first signs of arthritis 10 days after inoculating with mycobacterial arthritogen were then treated orally with the test materials for 4 days only. Effectiveness of the test materials was measured as increased rear paw thickness on day 14 when compared to the control group H.

The results are shown in Table 6 and indicate that PCO is more effective than indomethacin in this model.

TABLE 6

| Treatment | Dose Rate mg/kg | % Reduction in Inflammation |
|---|---|---|
| A. PCO | 5 | 91 |
| B. GL Mussel (NZ) | 300 | 21 |
| C. GL Mussel (Aust) | 300 | 97 |
| D. Celery Seed Oil | 3000 | 12 |
| E. Indomethacin ** | 5 | 83 |
| F. Indomethacin | 3 | 68 |
| G. Indomethacin | 1 | 26 |
| H. No treatment | | 0 |

** Toxic at this dose rate.

EXAMPLE 6

This Example provides further data comparing the effectiveness of the lipid extract of *Perna canaliculus* (PCO) when compared with freeze-dried whole mussel powder (Seatone™) and ibuprofen (Nurofen™), tested against collagen (II)-induced auto-allergic arthritis in rats. A gastro-toxicity assay was also carried out on the test materials.

Anti-arthritic Assay.

Collagen (Type II) induced polyarthritis was induced in female Wistar rats by injection of collagen (II) with a non-arthritogenic adjuvant to sensitise the test animals.

Table 7 shows results obtained in therapeutic (i.e. delayed) treatment with the test materials. The treatment was delayed until day 8 at the first signs of arthritis, then continued till day 14 (i.e. 7 daily doses) with the arthritis assessed on day 15 and again on day 18 —the latter indicating rebound on ceasing dosing. PCO was given orally after dilution into olive oil (8 mg/ml) and administered at 2.5 ml/kg/day to give 20 mg/kg.

The results show that PCO at 20 mg/kg is as effective in therapeutic treatment as 300 mg/kg stabilised mussel extract (Seatone) and 50 mg/kg ibuprofen (Nurofen).

Table 8 shows results obtained in both prophylactic and therapeutic treatment with the test materials. Prophylactic treatment was from day 1 to day 13 (i.e. total 15 doses) orally (p.o.). Therapeutic treatment was from day 9 to day 13 (i.e. total 5 doses) transdermally (t.d.). PCO was diluted into olive oil (6 mg/ml) for p.o. dosing at 2.5 ml/kg/day to give 15 mg/kg, and diluted into olive oil-cineole (17.3 v/v) (10 mg/ml) for t.d. administration at 2 ml/kg/day to give 20 mg/kg.

This experiment also included sodium aurothiomalate (ATM=Mycocrysin®) given as a reference anti-arthritic drug, administered every second day (total=8 doses) subcutaneously in saline at 6.3 mg/kg (higher doses were toxic). The relatively high weight gain of animals treated with ATM may be misleading, perhaps being a sign of incipient kidney damage (impaired urination), rather than a beneficial reduction in the normal weight loss associated with chronic inflammation.

Seatone™ was administered p.o. at 300 mg/kg; Nurofen™ was administered p.o. at 50 mg/kg; Na Aurothiomalate (ATM) was administered in 8 doses at 6.3 mg/kg subcutaneously (s.c.).

The results show that PCO is particularly effective when administered

Gastro-toxicity Assay

Gastro toxicity studies were carried out on female Wistar rats with established arthritis initiated with collagen (type II), not on drug therapy. Aspirin and PCO were suspended with 0.04% Tween-20 for oral dosing, after fasting animals overnight. Dose administered was 30 mg/kg.

Table 9 shows that PCO was virtually innocuous to the stomach even when given at 20 times an effective dose. This high dose (300 mg/kg) was however the effective dose for aspirin in the standard anti-arthritic assay (adjuvant-induced rat polyarthritis), at which dose aspirin can cause considerable gastric damage.

TABLE 7

| | | Mean Differences Days 8–15 | | | |
|---|---|---|---|---|---|
| Gp | Treatment | N/gp | †Rear L. Paw | †Rear R. Paw* | Ft. Paw Inflam. ΔWt |
| i | None | 4 | 1.77 mm | 1.62 mm | 2.5+ +10 gm |
| ii | Olive Oil only | 3 | 1.75 | 1.75 | 2.3+ +12 |
| iii | PCO/O.O | 4 | 0.32 | 1.04 | 0.6+ +20 |
| iv | Seatone (300 mg/kg) | 4 | 0.74 | 1.11 | 0.8+ +12 |
| v | Nurofen (40 mg/kg) | 3 | 0.82 | 1.48 | 0.7 + +15 |

| | % Inhibition | | | Differences Days 15–18 (Rebound) | | | |
|---|---|---|---|---|---|---|---|
| Gp | Rear L. paw | Rear R. paw | Front paw | Rear L. paw | Rear R. paw | Front paw | ΔWt. |
| i | — | — | — | 0.25 | 0.44 | 0.5+ | −03 |
| ii | 01 | (−8) | 08 | 0.05 | 0.55 | 0 | +02 |
| iii | 82 | 36 | 76 | 0.76 | 0.34 | + | +04 |
| iv | 58 | 31 | 68 | 0.64 | 0.22 | 1.2+ | +03 |
| v | 54 | 07 | 72 | 0.38 | 0.38 | 1.1+ | +05 |

*Right paw was pre-inflamed from original sensitising injection of collagen (II) in Freund's adjuvant.
Note:
Significant rebound in Gps (iii) and (iv) on ceasing dosing.

TABLE 8

| | | | Day 14: Signs arthritis | | | | |
|---|---|---|---|---|---|---|---|
| | | | Rear paw inflammation* | †Left | †Right | Front | |
| Gp | Treatment | N/Gp | Day 2 | Day 4 | rear paw | rear paw | paw inflam. | ΔWt(0–14) |
| I | None | 4 | 1.41 mm | 1.27 | 2.0 mm | 1.75 mm | 2.2+ | +07 gm |
| II | Seatone p.o.x15 | 4 | 1.07 | 0.93 | 1.14 | 1.51 | 2+ | +08 |
| III | PCO p.o.x15 | 4 | 1.06 | 0.80 | 1.25 | 1.69 | 0.8+ | +13 |
| IV | Nurofen p.o.x15 | 3 | 1.48 | 1.52 | 1.35 | 1.72 | 2.5+ | +12 |
| V | ATM s.c.x8 | 3 | 1.00 | 0.68 | 0.47 | 0.70 | 1.3+ | (+24) |
| VI | Oil/Cineole t.d.x5 | 4 | N.D. | | 1.84 | 1.30 | 1.9+ | +02 |
| VII | PCO/Oil Cineole t.d.x5 | 4 | N.D. | | 0.40 | 1.49 | 0.9+ | +08 |

| | "Rebound" (Day 18) | | | Percent Inhibitions | | | |
|---|---|---|---|---|---|---|---|
| Gp | Left rear paw | Right rear paw | Front paw Inflam. | 2 | 4 | †Left rear paw | †Right rear paw | Front paw inflam. |
| I | | | | — | — | — | — | — |
| II | | | | 24% | 27% | 43% | 14% | 09% |
| III | | | | 25 | 37 | 37 | 03 | 64 |
| IV | | | | (−05) | (−20) | 32 | 02 | (−14) |
| V | | | | 29 | 46 | 76 | 60 | 41 |
| VI | | | | N.D. | | 08 | 26 | 14 |
| VII | 0.57 | 0.29 | 1.4+ | N.D. | | 80** | 15** | 59** |

*Inflamed by injection of collagen (II) with a non-arthritogenic adjuvant to sensitise animals.
**Note significant rebound.

TABLE 9

| | Gastric lesion index | |
|---|---|---|
| RATS (n = 3/gp) | Aspirin | PCO |
| Low arthritis, Day 32 | 41 | 0 |
| High arthritis, Day 15 | 82 | 0 |
| High arthritis with 0.15 N HCl* | >112 | 06 |

* HCl co-administered orally to stimulate acid secretion under stress etc.

REFERENCES

1. Cullen, J. C., Flint, M. H. and Leider, J. (1975). N. Z. Med. J. 81: 260–261.
2. Miller, T. E. and Ormrod, D. J. (1980). N. Z. Med. J. 92: 187–193.
3. Winter, C. A., Risely, E. A. and Nuss, G. W. (1962). Proc. Soc. Exp. Biol. Med. 111: 544–547.
4. Rainsford, K. D. and Whitehouse, M. W. (1980). Arzneim.-Forsch./Drug Res. 30 (ii), 2128–2132.
5. Gibson, R. G., Gibson, S. L. M., Conway, V. and Chappel, D. (1980). The Practitioner 224:955–960.
6. Whitehouse, M. W. "Adjuvant-induced Polyarthritis in Rats", in Handbook of Animal Models for the Rheumatic Diseases, Vol. 1, pages 3–16, Editors R. A. Greenwald and H. S. Diamond, CRC Press, Inc., Boca Raton, Fla., USA.

What is claimed is:

1. A method of anti-inflammatory treatment of a human or animal patient, which comprises administration to the patient of an effective amount of a lipid extract of *Perna canaliculus* or *Mytilus edulis* rich in non-polar lipids, wherein said lipid extract is prepared by supercritical fluid extraction.

2. A method according to claim 1, wherein cryogenic fluid $CO_2$ is used in said supercritical fluid extraction.

3. A method according to claim 1 or claim 2, wherein said administration is oral or subcutaneous administration.

4. A method according to claim 1 or claim 2, wherein said administration is transdermal administration.

5. A method according to claim 1 or 2, wherein said anti-inflammatory treatment is treatment of arthritis, including rheumatoid arthritis and osteoarthritis.

6. An anti-inflammatory composition comprising a lipid extract of *Perna canaliculus* or *Mytilus edulis* rich in non-polar lipids as an active component thereof, wherein said lipid extract is prepared by supercritical fluid extraction, together with one or more pharmaceutically acceptable carriers and/or diluents.

7. A composition according to claim 6, wherein cryogenic fluid $CO_2$ is used in said supercritical fluid extraction.

8. A composition according to claim 6 or claim 7, wherein said composition is formulated for oral or subcutaneous administration of said active component.

9. A composition according to claim 6 or claim 7, wherein said composition is formulated for transdermal administration of said active component.

10. A composition according to claim 9, comprising an ointment or lotion base or vehicle, and optionally a skin penetration enhancing agent.

11. A composition according to claim 10, wherein said base or vehicle comprises an oil.

12. A composition according to claim 11, wherein said oil is olive oil or emu oil.

13. A composition according to claim 10, which includes a skin preparation enhancing agent.

14. A composition according to claim 13, wherein said agent is cineole or limonene.

* * * * *